(12) United States Patent
Sprichise et al.

(10) Patent No.: US 7,727,251 B2
(45) Date of Patent: Jun. 1, 2010

(54) LOW PROFILE DILATOR FOR ARTERIOTOMY CLOSURE SYSTEM

(75) Inventors: Matthew Spurchise, Peabody, MA (US); Juan-Pablo Mas, Somerville, MA (US); Jeffrey J. Witts, North Reading, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 498 days.

(21) Appl. No.: 11/739,980

(22) Filed: Apr. 25, 2007

(65) Prior Publication Data

US 2008/0269794 A1  Oct. 30, 2008

(51) Int. Cl.
*A61M 29/00* (2006.01)
(52) U.S. Cl. .................................................. 606/191
(58) Field of Classification Search ............. 604/96.01, 604/166.01, 505, 165.01, 164.1, 164.01, 604/534; 606/191, 213
See application file for complete search history.

(56) References Cited

U.S. PATENT DOCUMENTS

| 6,506,210 | B1 | 1/2003 | Kanner |
| 6,641,592 | B1 | 11/2003 | Sauer et al. |
| 6,767,356 | B2 * | 7/2004 | Kanner et al. ............... 606/213 |
| 7,074,232 | B2 | 7/2006 | Kanner et al. |
| 2001/0044594 | A1 * | 11/2001 | Martin et al. ............ 604/93.01 |
| 2007/0078478 | A1 * | 4/2007 | Atkins et al. ................ 606/191 |
| 2007/0185521 | A1 * | 8/2007 | Bui et al. ..................... 606/191 |

\* cited by examiner

*Primary Examiner*—Todd E Manahan
*Assistant Examiner*—Brian Graham

(57) ABSTRACT

A low profile, two lumen dilator is provided for an arteriotomy closure system. The dilator includes a first lumen adapted to receive a guidewire and a second lumen having a proximal segment that defines a blood marking lumen and a distal segment that receives the distal ends of stabilizers in a common pocket. The blood marking lumen and pocket are arranged in tandem. The guidewire lumen may extend the full length of the dilator or may be shortened to provide rapid exchange capability.

4 Claims, 4 Drawing Sheets

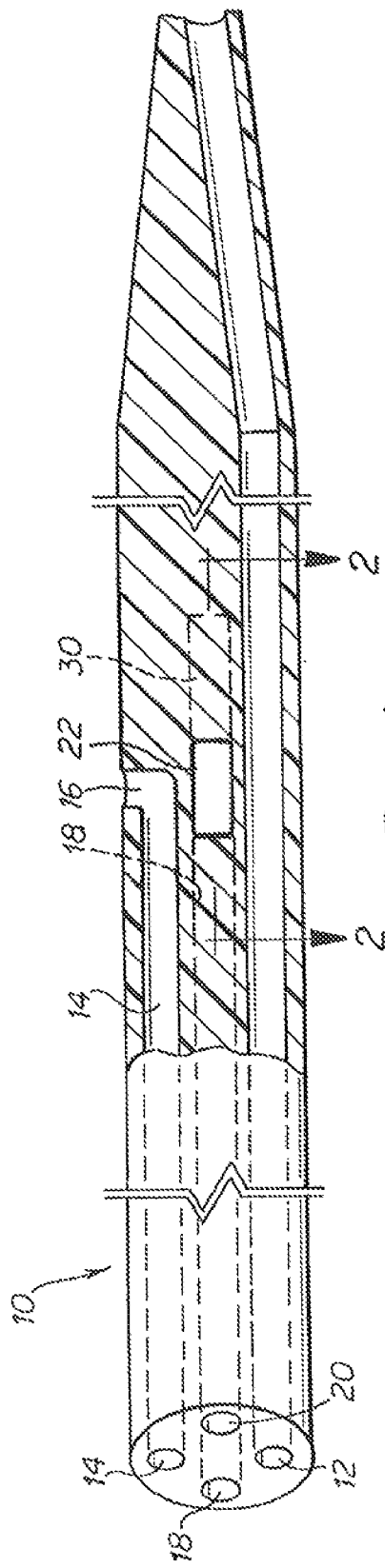
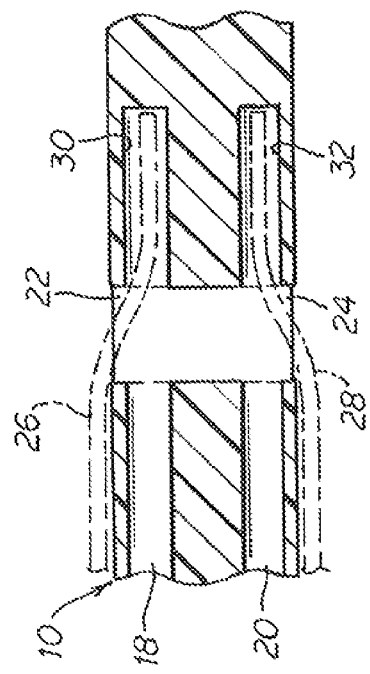
Fig. 1 PRIOR ART
Fig. 2 PRIOR ART

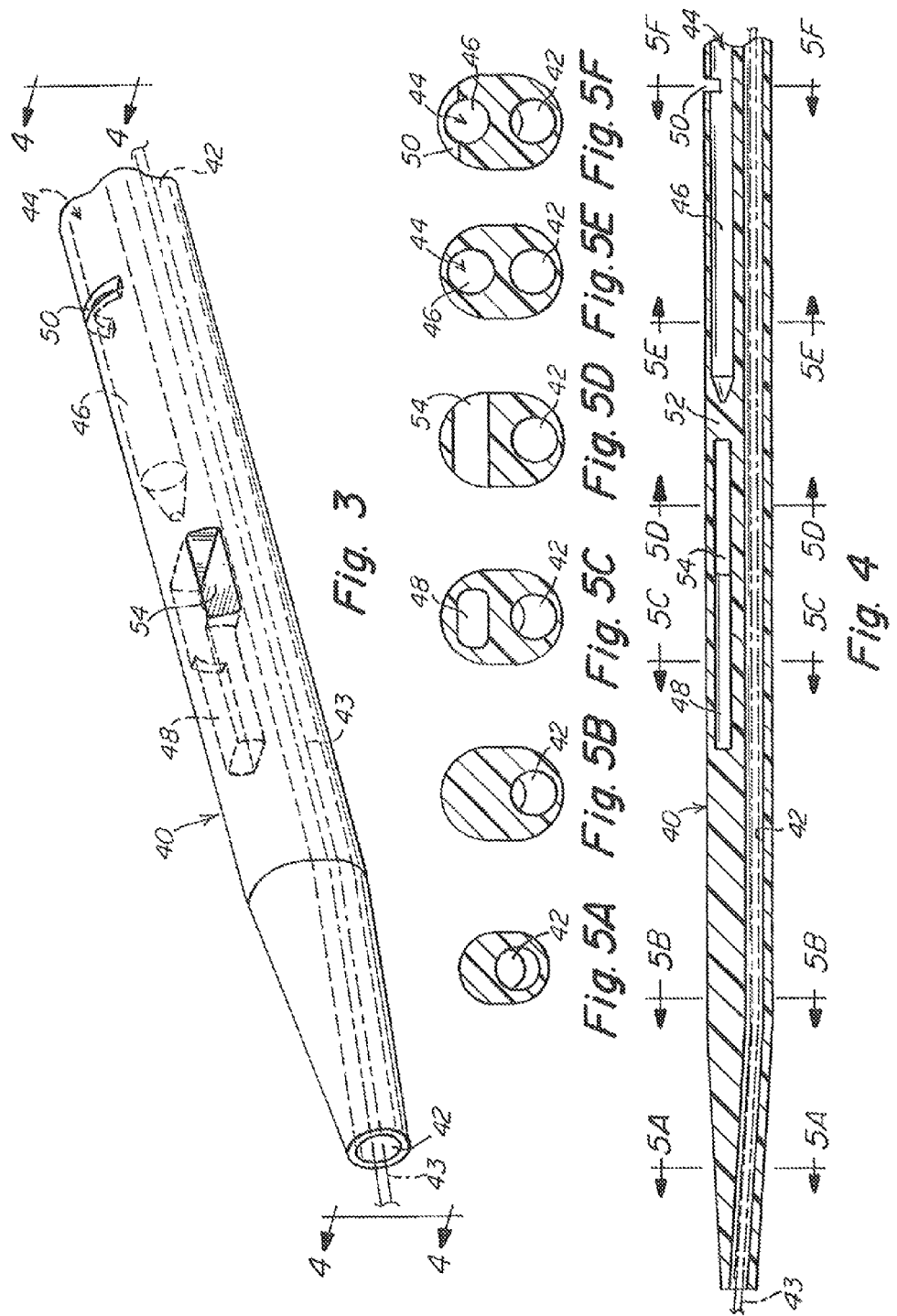

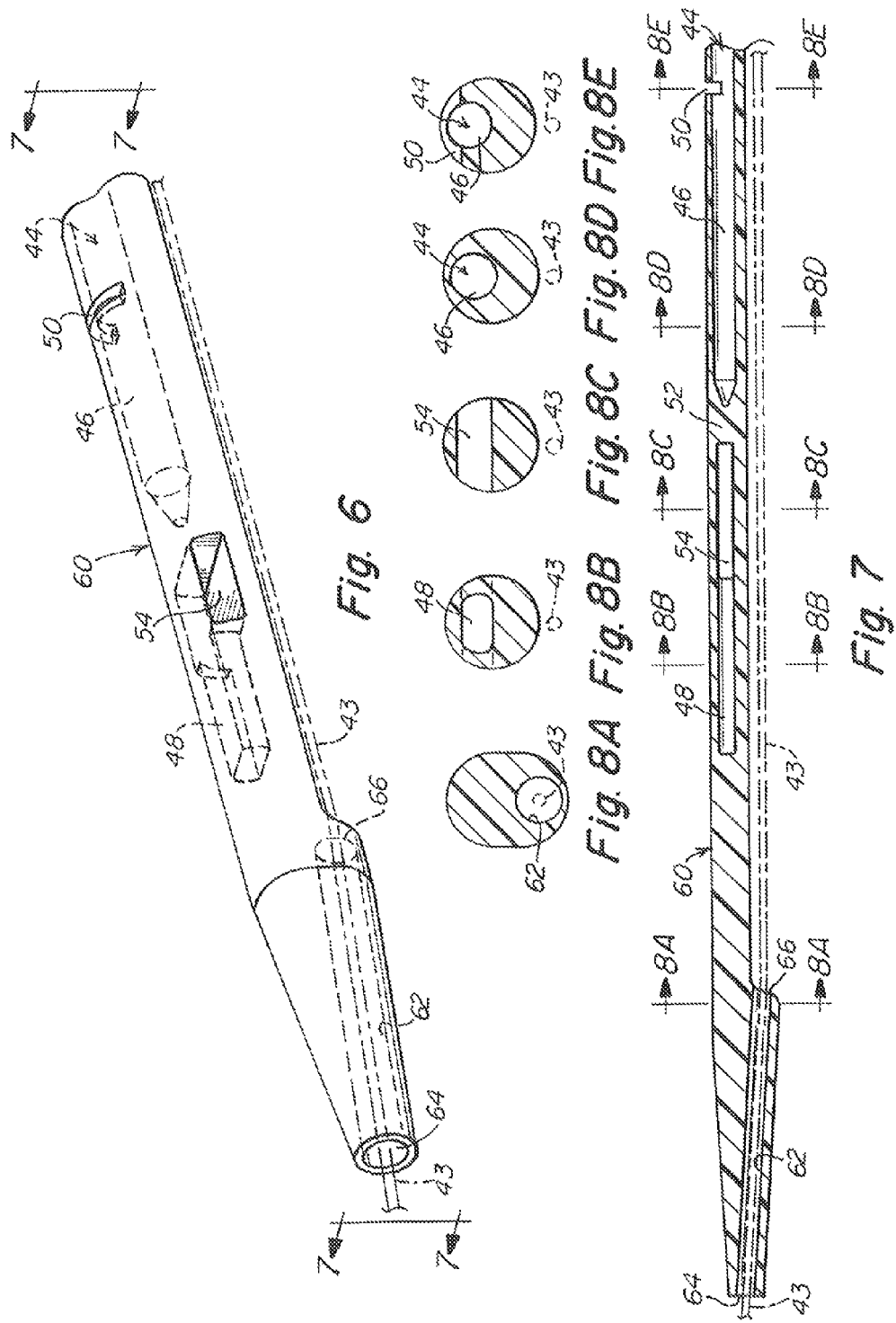

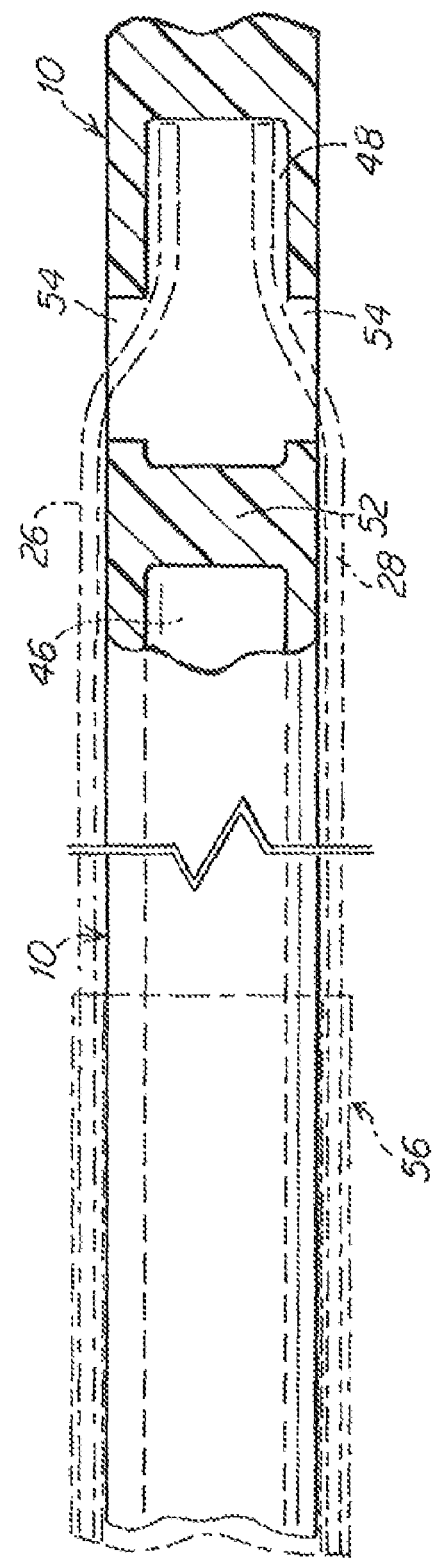

LOW PROFILE DILATOR FOR ARTERIOTOMY CLOSURE SYSTEM

FIELD OF THE INVENTION

The invention relates to devices for closing a percutaneous puncture in a blood vessel after an intravascular procedure and, particularly, to improved low profile dilators usable in the system.

BACKGROUND

Various cardiovascular procedures, such as angioplasty, stent placement and atherectomy, among others, are performed by inserting into and manipulating within the vasculature, wires and catheters adapted to perform those procedures. Access to the vasculature typically is through the femoral artery and is percutaneous, involving insertion of a needle in the region of the groin to form a track and to puncture and create an arteriotomy in the femoral artery. A guidewire then is advanced through the needle and into the femoral artery. The needle then is removed. An introducer sheath is then advanced over the guidewire. The wire and sheath provide access into the femoral artery, through the arteriotomy, for catheters or other instrumentalities in order to perform the selected procedure.

After the procedure has been completed, the procedural devices are removed and the arteriotomy must be closed. A number of techniques are known to facilitate closure and healing of the arteriotomy. These include application of pressure at the puncture site for a relatively extended length of time or the use of biological adhesives or plugs adapted to seal the arteriotomy, among others. Also among the techniques for closing the arteriotomy is the use of a staple system such as described in U.S. Pat. Nos. 6,506,210, 6,767,356 and 7,074,232 to Kanner et al., of which the disclosures of the devices and methods are hereby incorporated by reference. The Kanner patents described a system by which the original introducer sheath is removed, leaving the guidewire in place. Then, an assembly that includes a closure sheath and dilator is advanced along the indwelling guidewire to bring the distal end of the closure sheath into proximity to the outer surface of the arteriotomy. The closure sheath also carries an arrangement of display extending, wire-like stabilizers that, together with the dilator, pass through the arteriotomy into the artery.

The free ends of the stabilizers extend beyond the distal end of the closure sheath and are retained within pockets formed in the sides of the dilator to prevent the ends from interfering with advancement of the dilator or closure sheath through tissue.

The system enables the portions of the stabilizer wires, once disposed within the artery, to be formed into a temporarily enlarged shape that prevents removal of the stabilizer wires through the arteriotomy. The stabilizers and distal end of the closure sheath then are drawn together to grip the tissue about the arteriotomy and thereby secure and fix the position of the distal end of the sheath over and in alignment with the arteriotomy. The dilator and guidewire then are removed through the closure sheath, leaving the sheath in place adjacent the outer surface of the artery with the stabilizers within the artery, holding the sheath in place in readiness to provides direct access to the arteriotomy.

An arteriotomy closure device, such as a catheter-like stapler, with a staple carried in its distal end, then is inserted into and advanced through the closure sheath to located the staple in proximity to the arteriotomy. As described more fully in the Kanner patents, the sheath and stabilizer mechanisms orient the staple in registry with and at a fixed distance from the arteriotomy. When the stapler is actuated, the prongs of the staple expand and advance toward and into the arterial wall and surrounding tissue on opposite sides of the arteriotomy. The stapling mechanism then draws the prongs of the staple together to draw the edges of the arteriotomy together into approximation and then releases the staple. The stabilizers are caused to return to a linear shape, enabling their withdrawal. With the staple deployed and having closed the arteriotomy, the stapling mechanism and sheath may be removed, leaving the staple in place.

The dilator described in Kanner U.S. Pat. No. 6,767,356 is circular and has four separate lumens, including a guidewire lumen, a blood marking lumen, and a pair of side lumens. The distal ends of the side lumens server as pockets to temporarily receive the distal ends of the stabilizers when the dilator and closure sheath are advanced through tissue. The dilator includes side port openings in it sides, just beyond the distal end of the sheath, through which the distal ends of the stabilizers can be placed within the pockets. The portions of the side lumens proximal of the side ports, although useful in forming the stabilizer pockets, performed no function during operation or use of the system. It would be desirable, therefore, to provide a dilator for use in the arteriotomy closure system that omitted the proximal side lumens. The resulting dilator thus could have a lower profile or, alternatively, would enable the dilator or closure sheath to be further modified to include other operating functions and elements.

SUMMARY OF THE INVENTION

The modified dilator is formed to include two lumens, including a first lumen receptive to a guidewire, and a dual-function second lumen that is employed both as a blood marking lumen and as a pocket region to releasably receive the distal ends of the stabilizers. The second lumen may be considered as having a proximal segment that defines the blood marking lumen and a short distal segment in which side ports are formed to receive the distal ends of the stabilizers. The invention utilizes a single stabilizer pocket adapted to receive, through the side ports, and contain the distal ends of both stabilizers. The proximal and distal segment of the second lumen are aligned axially such that the common stabilizer pocket and blood marking lumen are arranged in tandem.

In one embodiment, the guidewire lumen may extend from the distal tip of the dilator along the full length of the dilator to the proximal end, the dilator maintaining a uniform outer cross-sectional configuration. In another embodiment, the guidewire lumen is relatively short and located at the distal tip of the dilator, with a proximal guidewire port defining the proximal extend of the guidewire lumen. Catheters having such short distal guidewire lumens are typically referred to as "rapid exchange" devices because of their ability to be removed and/or replaced over standard-length guidewires instead of requiring extra-long "exchange" guidewires. This conventional "rapid exchange" language will be used to describe one embodiment throughout the description of the invention, even though the short guidewire lumen feature is not used for exchanging the inventive dilator. The more proximal portions of the rapid exchange embodiment of the dilator contain only the single, second lumen.

DESCRIPTION OF THE DRAWINGS

The invention will be appreciated more fully from the following further description with reference to the accompanying drawings wherein:

FIG. 1 is a diagrammatic illustration of a four-lumen dilator used in arteriotomy closure system described in Kanner U.S. Pat. No. 6,767,356;

FIG. 2 is a fragmented sectional illustration of a portion of the dilator of FIG. 1 as seen along the line 2-2 of FIG. 1;

FIG. 3 is an isometric, somewhat diagrammatic, illustration of one embodiment of a two-lumen dilator in accordance with the invention;

FIG. 4 is a longitudinal cross-section of the dilator of FIG. 3 as seen along the plane 4-4 of FIG. 3;

FIGS. 5A-5F are sectional illustrations of the dilator of FIG. 4 as seen along the section planes 5A-5F of FIG. 4;

FIG. 6 is an isometric illustration of another embodiment of a two lumen dilator incorporating a rapid exchange guidewire lumen in accordance with the invention;

FIG. 7 is a sectional illustration of the dilator of FIG. 6 as seen along the plane 7-7 of FIG. 6;

FIGS. 8A-8E are sectional illustrations of the dilator of FIGS. 6 and 7 as seen along the planes 8A-8F of FIG. 7; and FIG. 9 is a diagrammatic illustration of the manner in which the distal ends of the stabilizers are contained in the common pocket of the dilator.

DESCRIPTION OF THE PREFERRED EMBODIMENT

FIGS. 1 and 2 illustrate a dilator 10 of the type described in '356 Kanner patent. The dilator is formed from a somewhat flexible biocompatible polymer and is formed with four lumens including a guidewire lumen 12 that extends the full length of the dilator, a blood marking lumen 14 that extends from the proximal end to a blood marking port 16 located proximally of the distal end of the dilator and a pair of laterally spaced lumens 18, 20. Each side lumen 18, 20 communicates with side ports 22, 24 respectively in a distal segment of dilator 10. Side ports 22, 24 may be cut or otherwise formed in the dilator. Each side port is adapted to receive the distal end of a stabilization wire, shown in phantom diagrammatic fashion at 26, 28 with the distal ends of the stabilization wires being received in separate distal pockets 30, 32. The distal pockets 30, 32 are formed as continuations of the side lumens 18, 20. The cross-section of the dilator is circular and is large enough to accommodate all four lumens along substantially the full length of the dilator.

FIGS. 3, 4 and 5A-5F illustrate one embodiment of a modified dilator in accordance with the invention. The dilator has a shaft 40 formed with two lumens including a first lumen 42 adapted to receive a guidewire, illustrated diagrammatically in phantom at 43, and a dual-function second lumen 44 that serves to define both a blood marking lumen 46 as well as a single, common pocket 48 to received the distal ends of the stabilizers. The guidewire lumen 42 extend the full length of the dilator from an outlet port at the tapered distal end of shaft 40 to the proximal end of shaft 40. The blood marking lumen 46 includes a port 50 near the distal end of the lumen. The distal end of the blood marking lumen may be formed by a plug or composition inserted into the region 52 to separate the blood marking lumen 46 from the more distal portions of the second lumen 44. Alternatively, shaft 40 may be formed by joining different extruded or molded shaft segments, as by melt bonding or adhesive bonding, to form the required lumens and cross-sectional shapes and sizes. A transverse opening is formed through the dilator in communication with the common pocket 48 to define a pair of opposed side ports 54 for the stabilizers. The portion of the second lumen 44 extending distally beyond the side ports 54 define the common pocket 48 to receive and contain the distal ends of both stabilizers.

FIG. 9 illustrates, diagrammatically, the manner in which the distal ends of the wire-like stabilizers extend into and are contained within the distal common pocket. The stabilizers extend distally from the sheath 56 and along the sides of the dilator, passing through the side ports 54 and into the common pocket 48 distally of the side ports. The distal ends of the stabilizers are contained within the common pocket during advancement of the system to a deployment position. As described in further detail in the Kanner '356 patent, the dilator then is advanced distally to enable the distal ends of the stabilizers to be withdrawn from the pocket and out of the side ports, after which the stabilizers can be actuated to the stabilizing configuration.

FIGS. 5A-5F illustrate sections taken along the length of the dilator from which it may be seen that the dilator may be configured to an oval configuration to an oval configuration. The invention enables the dilator to be formed with an oval cross-section that results in reduction in the cross-sectional dimensions and profile as compared to a circular four-lumen dilator.

FIGS. 6, 7 and 8A-8E illustrate another embodiment of the invention in which the two lumen dilator shaft 60 comprises a rapid exchange guidewire lumen 62. In this embodiment, the guidewire lumen 62 extends from the distal outlet port 64 to a proximal guidewire port 66 located distally of the distal end of the stabilizer pocket 48. With this arrangement, a portion of the guidewire, illustrated diagrammatically in phantom at 43 extending proximally from the proximal guidewire port is disposed outside of the dilator. The dilator shaft 60 in this embodiment, from the proximal guidewire port 66 to the proximal end of the dilator may be of further reduced in cross-sectional configuration and may be circular as shown.

It should be understood that the foregoing description of the invention is intended merely to be illustrative thereof and that other embodiments, modifications and equivalents may be apparent to those skilled in the art while remaining within the scope of the invention.

We claim:

1. In a wire-guided arteriotomy closure system having a sheath and stabilizers extending distally from the sheath, a low profile dilator for placing the sheath and stabilizers with respect to an arteriotomy comprising:

an elongate dilator shaft having a tapered distal end, the dilator shaft having a first guidewire lumen and a second lumen parallel to the first lumen;

the second lumen having a proximal segment defining a blood marking lumen extending from the proximal end of the dilator to a blood marking port at the distal region of the proximal segment of the second lumen;

the second lumen having a distal segment, the dilator shaft having a pair of side ports formed therein and in communication with the distal segment of the second lumen with a portion of the second lumen extending distally beyond the side ports to define a distally extending pocket receptive to the ends of wire-like stabilizers;

the proximal and distal segments of the second lumen being separated by a plug or composition and being arranged in tandem such that the transverse cross-section of the dilator, over substantially all of its length, has not more than two lumens.

2. A low profile dilator as defined in claim 1 wherein the first guidewire lumen extends the full length of the dilator.

3. A low profile dilator as defined in claim 1 wherein the guidewire lumen extends from a distal guidewire port to a proximal guidewire port, the proximal guidewire port being located distally of the pocket and enabling the dilator to be operated as a rapid exchange device.

4. A low profile dilator as defined in claim 1 wherein the transverse cross-section of the dilator, over substantially all of its length, is oval.

* * * * *